United States Patent
Speitling et al.

(10) Patent No.: US 7,763,022 B2
(45) Date of Patent: Jul. 27, 2010

(54) LOCKING NAIL FOR TREATING FRACTURES OF THE PROXIMAL FEMUR

(75) Inventors: Andreas Werner Speitling, Kiel (DE); Klaus Dorawa, Kiel (DE); Geert Von Oldenburg, Heikendorf (DE)

(73) Assignee: Stryker Trauma GmbH (DE)

( * ) Notice: Subject to any disclaimer, the term of this patent is extended or adjusted under 35 U.S.C. 154(b) by 113 days.

(21) Appl. No.: 10/771,253

(22) Filed: Feb. 3, 2004

(65) Prior Publication Data

US 2004/0172027 A1    Sep. 2, 2004

(30) Foreign Application Priority Data

Feb. 7, 2003    (DE) .................. 203 01 902 U

(51) Int. Cl.
*A61B 17/72* (2006.01)

(52) U.S. Cl. ........................ 606/64; 606/329

(58) Field of Classification Search ............ 606/62–68, 606/300, 329, 98, 280, 282, 286
See application file for complete search history.

(56) References Cited

U.S. PATENT DOCUMENTS

| | | | | |
|---|---|---|---|---|
| 5,176,681 A | | 1/1993 | Lawes et al. | |
| 5,346,492 A | * | 9/1994 | Morgan | 606/60 |
| 5,374,235 A | * | 12/1994 | Ahrens | 606/101 |
| 5,472,444 A | * | 12/1995 | Huebner et al. | 606/64 |
| 5,733,287 A | * | 3/1998 | Tepic et al. | 606/69 |
| 5,743,908 A | * | 4/1998 | Kim | 606/64 |
| 6,224,601 B1 | * | 5/2001 | Friedl | 606/64 |
| 6,808,527 B2 | * | 10/2004 | Lower et al. | 606/62 |
| 6,942,665 B2 | * | 9/2005 | Gambale | 606/69 |
| 2002/0173792 A1 | * | 11/2002 | Severns et al. | 606/62 |
| 2003/0073999 A1 | * | 4/2003 | Putnam | 606/62 |
| 2004/0172026 A1 | * | 9/2004 | Ekholm et al. | 606/62 |
| 2004/0172027 A1 | | 9/2004 | Speitling et al. | |

FOREIGN PATENT DOCUMENTS

| | | |
|---|---|---|
| DE | 43 18 150 A1 | 12/1994 |
| DE | 43 41 677 C1 | 7/1995 |
| DE | 203 01 902 U1 | 6/2003 |
| GB | 2209947 | 6/1989 |
| WO | WO-01 39679 A1 | 6/2001 |

\* cited by examiner

*Primary Examiner*—Eduardo C Robert
*Assistant Examiner*—Mary Hoffman
(74) *Attorney, Agent, or Firm*—Lerner, David, Littenberg, Krumholz & Mentlik, LLP

(57) ABSTRACT

An interlocking nail, particularly for fractures of the proximal femur having a proximal portion that has provided therein a bore preferably extending obliquely to the axis of the proximal portion for receiving a screw or pin, particularly a femoral neck pin. The bore is formed so that the lateral edge portions located on opposed sides are flattened and rounded at the inlet end or also the outlet end of the bore.

7 Claims, 3 Drawing Sheets

LOCKING NAIL FOR TREATING FRACTURES OF THE PROXIMAL FEMUR

BACKGROUND OF THE INVENTION

The invention relates to an interlocking nail, particularly for fractures of the proximal femur.

For a repair of trochanteric fractures and fractures of the femoral neck or femoral head, it is known to provide an interlocking nail which is driven into the femur from the proximal end and, in a an oblique through bore, guides a femoral neck pin which is introduced into the femoral head via the femoral neck of the femur. It is known to provide the femoral neck pin with a thread to allow it to be screwed into the femoral head (femoral neck screw); however, it is also known to design the femoral neck pin as a blade. In the proximal part of the interlocking nail, it is further known to provide a bore which interacts with the femoral neck pin in such a way that it can axially move in the oblique through bore, but cannot rotate. Such a nail is shown in U.S. Pat. No. 5,176,681.

The weight force of a patient who is provided with such an implant is essentially directed into the interlocking nail from the femoral neck pin. The nail cross-section, when under a load, is subjected to a combined stress which is composed of bending and tensile stresses. In case of an overload, a crack or fissure may develop, namely at the site at which the highest tensile stress occurs. The highest concentration of stress results on the sharp lateral edges on opposed sides of the femoral neck pin when it is in the oblique through bore. Thus, the so-called fatigue strength of the implant depends on the critical area having edges with a sharp-edged geometry. The highest tensile stresses occur at the screw inlet end of the bore.

SUMMARY OF THE INVENTION

It is one object of the invention to improve an interlocking nail of the aforementioned type by enhancing its fatigue strength.

An interlocking nail of the present invention has an edge formed around an oblique through bore formed in the interlocking nail. The edge may have four portions. Regarding the individual edge portions at the inlet end of the bore, the edge portions directed towards the proximal and distal ends of the nail are discriminated from those which are located towards the sides of the nail. In the interlocking nail of the present invention, the edges located towards the sides of the nail are flattened at the inlet end and/or outlet end of the bore to form flattened edge surface portions. The edge portions directed towards the distal and proximal ends of the nail are rounded. It is preferred that the surface portions defined by the rounded edges in the distal and proximal end areas are formed to be essentially concave in a side view.

The edge portions located towards the sides of the nail, for known nails, constitute the most critical portions for a load because they are in an area of reduced cross-section. In the invention, some material is removed from these edge portions in a way that avoids a notch effect and, hence, the risk of stress peaks forming in this area. Load-bearing capacity increases although material is removed. In addition, this essentially maintains the entire support area for the pin in the hole, particularly that of the femoral neck pin in the oblique through bore as is predetermined by the geometry of the nail and bore.

It is possible to provide for the removal of material by flattening the aforementioned edge. However, according to an aspect of the invention, it is preferred that a notch be formed which machines the entire edge at least of the inlet end, to define flattened edge portions located towards the sides of the nail. Also, it may be configured in geometry so as to maintain the sliding surface of the pin essentially over the entire length.

Preferably, the outer perimeter of the notch is rectangular or square and has rounded corners.

The relatively narrow, elongate surface portions on the opposed lateral edge portions preferably pass over, towards the proximal and distal sides of the inlet end or outlet end, into rounded surface portions which exhibit a concave run as seen from the side.

The invention is particularly useful for interlocking nails which receive a femoral neck pin in a proximal oblique hole. Also, the inventive relief of stress from the inlet end of the oblique hole is sufficient here. However, it is also suited for holes of the interlocking nail which are perpendicular to the nail axis and are distally disposed.

In the nail of the present invention, the fatigue strength of the implant is enhanced by varying the external geometry of the bore at the ends so as to bypass the stresses provoked by the load when in a clinical use. Critical areas are relieved of stress that arises because of sharp-edged geometries. The sharp edges are removed and the stress is spread over a larger surface. This advantage is attained with no harm caused to the sliding mechanism for the pin.

As discussed above, the stress lines run along the weakest cross-section in a through bore of a nail. By flattening the lateral edge portions of the inlet end of the oblique hole, the stress lines are bypassed around the cross-section in the area of higher strength. In another embodiment (FIG. 8), a provision can be made here to chamfer or bevel the circumferential edge by the removal of material at the inlet end of the bore over its entire perimeter. At this stage, the invention provides for the circumferential edge of the inlet area to present a circumferential chamfer or inclined surface the shape and run of which is formed by the fact that a circular milling cutter, which is rotated about its axis which is perpendicular to the axis of the proximal nail portion and the diameter of which is larger than the diameter of the bore, it is moved against the edge of the inlet end until the circumferential chamfer is produced. In this manner, an efficient relief from stress is also achieved in the inlet end of the bore with the material not being unfavorably weakened or the support surface of the femoral neck pin or other pin in the bore being diminished. Thus, the step of manufacture, which is required to produce the stress reduction can be accomplished by simple means.

These and other objects of the invention are achieved by a nail for insertion into the medullary canal of the long bone, such as a femur, which nail has an elongated shank extending along the longitudinal axis from a first and to a second end of the nail shank. A cross-bore extends through the nail shank along an axis transverse to the longitudinal axis. The cross-bore is for receiving a bone fastener, such as a bone screw or a bone pin from an inlet side of the cross-bore to an outlet side thereof. When used in conjunction with the femur, the cross-bore may be at an oblique angle and extend through the proximal end of the nail into the head of the femur. An outer surface surrounding the bore inlet end has recessed edges along first and second sides thereof with at least central portions of the recessed edges being substantially planar and extending in a plane generally parallel to the longitudinal axis of the shank. Where the recessed edges intersect the edges of the throughbore, the sharp corners may be relieved such as by rounding or blending the recessed edge into the inner bore.

The recessed edges form first and second sides of a notch in the outer surface surrounding the bore with the first and second recessed edges being connected by a third side of the notch with the third side extending in a direction generally perpendicular to the nail axis. Preferably, the third side is rounded. When the nail is a femoral nail, the rounding is at least on the distal side of the outer surface surrounding the bore. The first and second recessed sides are also connected by a fourth side located closer to the first end of the nail, which, in the femur is the proximal end. The fourth side may also be rounded. The first and second sides have portions which are parallel and, similarly, the third and fourth sides have edges which are parallel to each other. Preferably, the parallel portions of the first and second sides are perpendicular to the parallel portions of the third and fourth sides.

BRIEF DESCRIPTION OF THE DRAWINGS

The invention will be described in more detail below with reference to an embodiment shown in the drawings.

DESCRIPTION OF THE PREFERRED EMBODIMENTS

Figure 1:
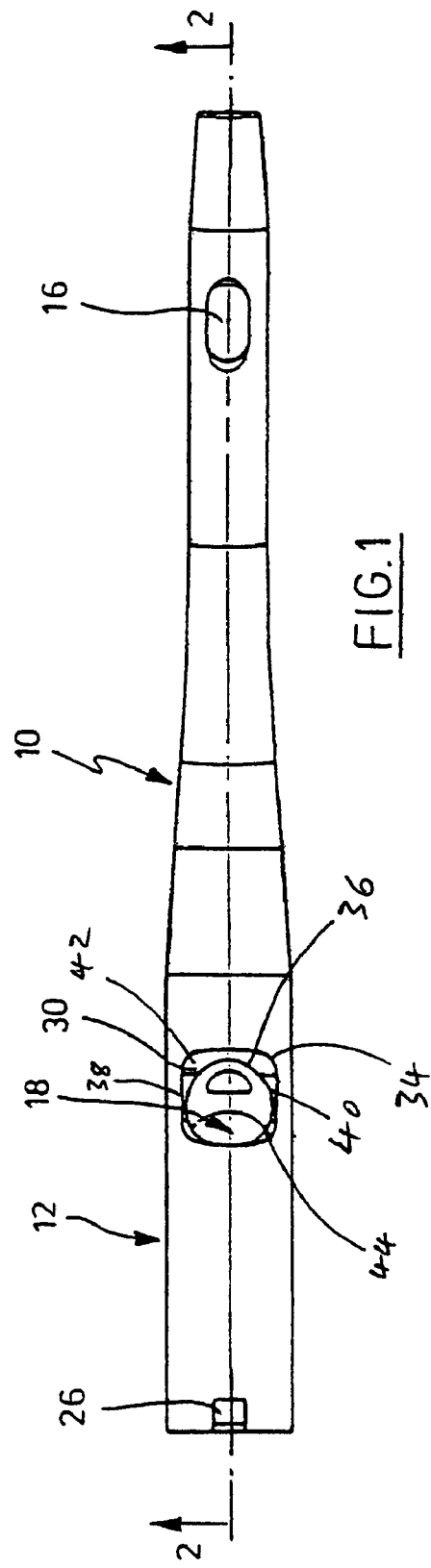
FIG. 1 shows the plan view of an interlocking nail according to the invention.
Figure 2:
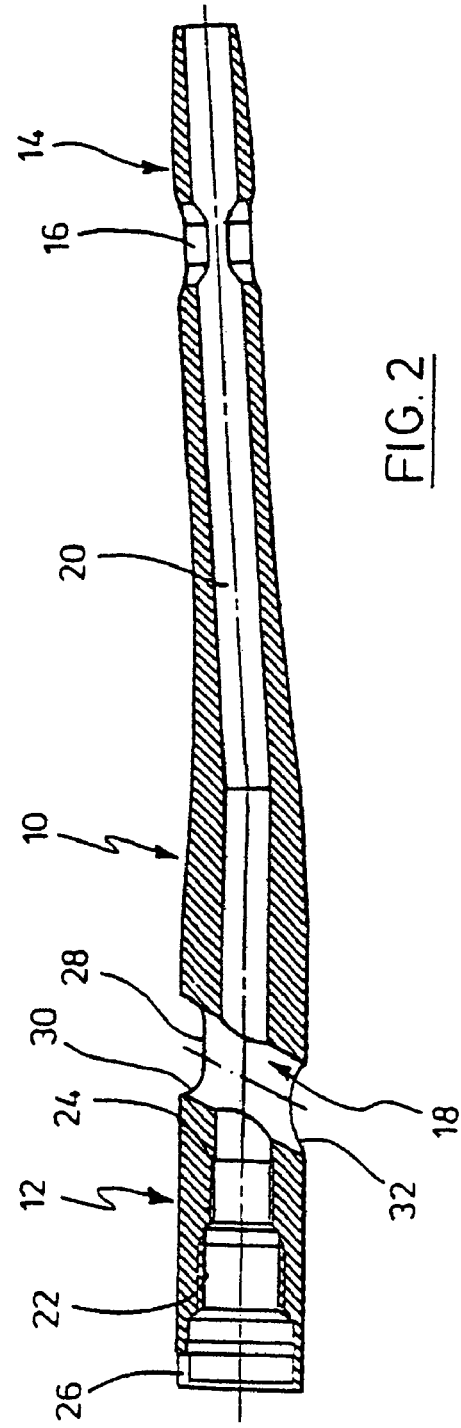
FIG. 2 shows a section through the nail of FIG. 1 along line 2-2.

An interlocking nail 10 as is illustrated in FIGS. 1 and 2 has a proximal portion 12 and a distal portion 14. The latter contains an elongate cross-bore 16 for receiving an interlocking screw which is not shown. The proximal portion has an oblique through bore 18 for receiving a femoral neck pin which is not shown. Reference was made above and will always be made below to a femoral neck pin although it is intended to generally comprise all common femoral neck screws and pins that have become known up to this date.

The nail 12 is completely formed with an axial through bore 20 and the proximal end has provided thereon two threaded portions 22, 24 which are different in diameter, the internal one 24 serving for the reception of an interlocking pin or set screw, which is not shown, for the femoral neck pin and the thread 22 serving for the reception of an insertion and targeting instrument, which is not shown, for fixing the nail via the proximal femur. A radial recess 26 at the proximal end serves for orienting the insertion and targeting instrument on the nail 10 in a rotary sense. These constructional features mentioned are known in the state of the art. The description which follows is focused on the oblique bore 18. As shown FIGS. 3 and 6, bore 18 may be circular. Bore 18 has an inlet end 30 and an outlet end 32 for the femoral neck pin. The inlet end faces away from the head of the femur when the nail has been driven into the femur proximally. The considerations below exclusively refer to the inlet end which can be recognized in FIG. 1, but is depicted more distinctly in FIGS. 3 and 4.

Figure 3:
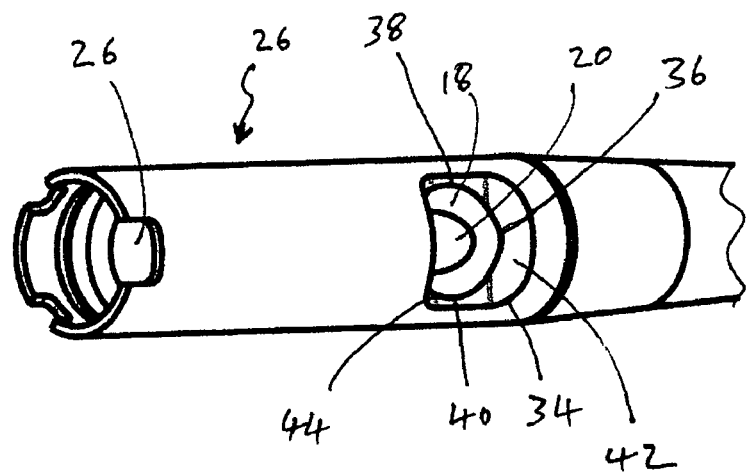
FIG. 3 shows the enlarged plan view of proximal portion 12 of the nail of FIG. 1 as seen from perspective A shown in FIG. 2 that is roughly 30 degrees from the vertical in counterclockwise direction.
Figure 4:
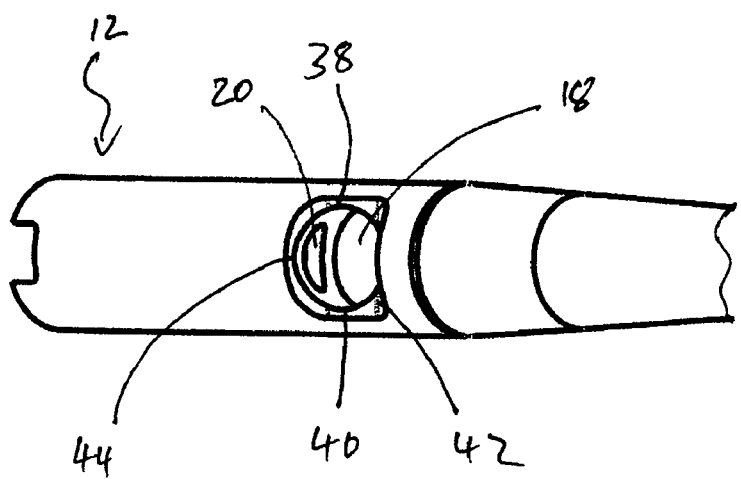
FIG. 4 shows a plan view of proximal portion 12 of nail of FIG. 1 (similar to FIG. 3), but from a perspective B Shown in FIG. 2 that is—offset by roughly 90° from perspective A, i.e., a perspective that is roughly 60 degrees from the vertical in clockwise direction.
Figure 5:
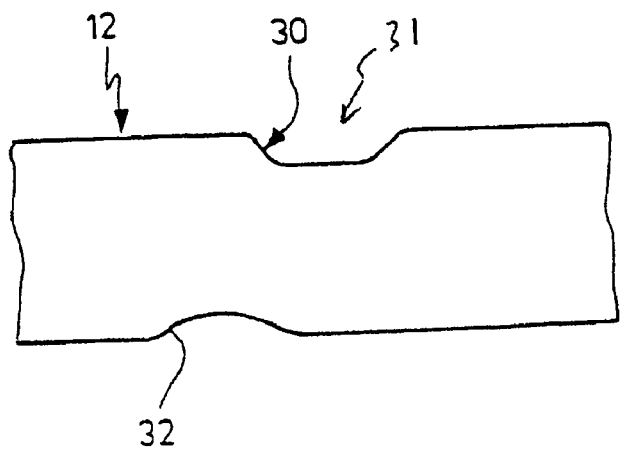
FIG. 5 shows the side view of the nail portion of FIG. 3.

As shown in the Figures the area of the inlet end 30, in a plan view, has formed therein a notch 31 (FIG. 5) the outer edge 34 of which has an approximately square contour with rounded corners. The edge 34 is outside the edge which is formed by the bore 18. The inner edge of the notch 31 which is radially located within the outer edge 34, which is formed by the intersection with bore 18, is designated by 36. Surface portions which are flattened and surface portions that are rounded are formed between the outer edge 34 and the inner edge 36. Flattened lateral surface portions 38, 40 are located on opposed sides of the femoral neck pin and, in a plan view, extend approximately in parallel (in same direction) with the outside of proximal nail portion 12. As evident from FIGS. 1 and 2 surface portions 38, 40 are located, at least in their middle region, approximately in a common plane which extends approximately in parallel with the longitudinal axis of proximal nail portion 12. The surface portions 38, 40 continue into surface portions 42, 44 in both the proximal and distal directions respectively. As shown in FIG. 3, surface portion 42 is distal and the surface portion 44 is proximal. As can be seen from FIG. 2 the shape of the contour of the surface portions 38, 40 is lightly concave in cross-section at the ends. The outer proximal edge portion essentially matches the shape of the edge portion which is formed by the bore 18.

The above described configuration of the notch 31 to be made in the oblique hole 18 in the inlet area for the femoral neck pin can be produced by a relatively easy manufacturing technique. The notch 31 ensures a marked reduction of the stress peaks in the end portions of the bore 18 when the femoral neck pin in the bore 18 is loaded by the force of the patient's weight, specifically at the inlet end, with no noticeable reduction to the sliding surface of the femoral neck pin, i.e. the support surface for the femoral neck pin in the oblique bore 18. The removal of material from the inlet end 30 can be readily seen from FIG. 5. The line of penetration of the oblique bore 18 in the outer contour of the proximal nail portion 12 has undergone a variation as seen from outlet end 32 because of the removal of material from and the flattening of the edge areas of the inlet end 30. It can be appreciated that relatively little material was removed so that the weakening of the material is negligible and is greatly outweighed by the advantages of favorable force transfer into the nail from the femoral neck pin. It is the surface portions 38, 40 which are vital for the reduction of the stress peaks.

Figure 6:
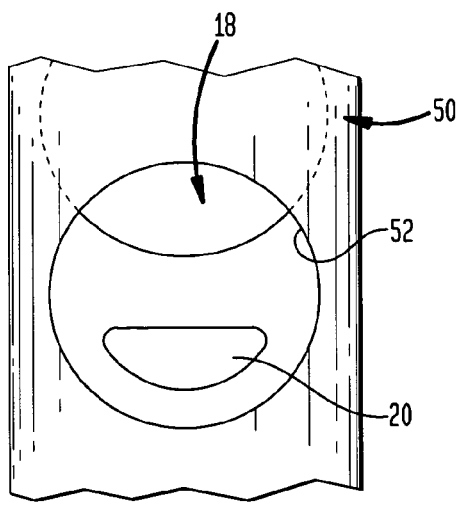
FIG. 6 shows a plan view of a proximal portion of a bone nail similar to the proximal portions of FIGS. 3 to 5 with an oblique through bore according to the state of the art.
Figure 7:
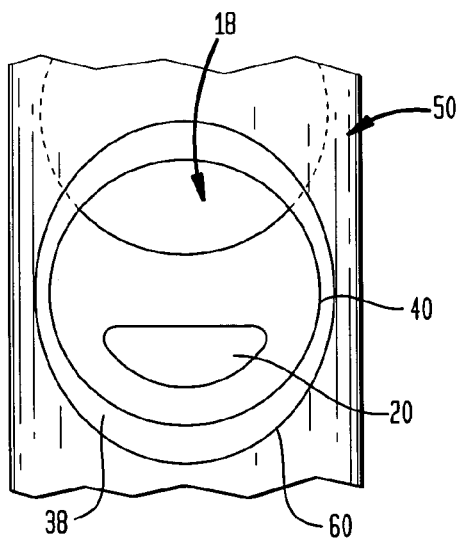
FIG. 7 shows the same view after making a chamfer on the circumferential edge of the inlet end of the oblique bore shown.
Figure 8:
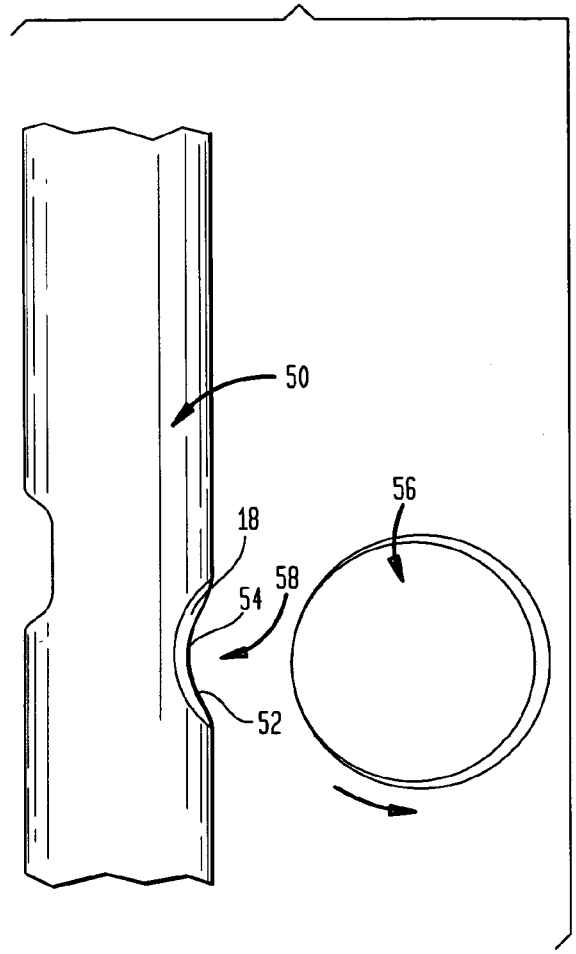
FIG. 8 shows a side view of the nail portion of FIG. 7

FIGS. 6 to 8 illustrate a proximal nail portion 50, e.g. that portion 12 of the femoral nail of FIGS. 1 and 2. FIG. 6 shows a conventional interlocking nail. FIGS. 7-8 show a second embodiment of the interlocking nail of present invention. FIGS. 6 and 7 each show the proximal end towards the top of the page whereas the distal end points towards the bottom of the page. The oblique hole is also referred to as 18. Likewise, the axial through bore is designated by the same reference number 20 as in FIGS. 2 to 4. The direction of sight of the views of FIGS. 6 and 7 is perpendicular to the nail longitudinal axis. FIG. 6 shows the nail portion 50 immediately after the manufacture of the oblique through bore and axial through bore 20. FIG. 7 shows the deformation of the circumferential edge 52 of the inlet end after undergoing chamfering by a milling cutter as this will be described below with reference to FIG. 8.

FIG. 8 shows the side view of the nail portion 50 approximately perpendicular to the oblique through bore 18 with the nail portion 50 having been rotated clockwise by about 5°, however. This allows a clear view of the run of edge 52 at inlet end 54 of the oblique bore 18. FIG. 8 further shows a circular milling cutter 56 which is rotated about an axis which is perpendicular to the longitudinal axis of the nail portion 50. The axial extension of the milling cutter 56 is larger than is the diameter of the oblique bore 18. The diameter of the circular milling cutter 56 is also larger than is the diameter of the oblique bore 18. During machining, the milling cutter is moved towards the edge 52 in the direction of the arrow 58. At this point, the milling cutter 56 plunges into the inlet end 54 of the bore approximately centrally and chamfers the circumferential edge 54 circumferentially as can be seen at 60 in FIG. 7. Also here, in particular, lateral opposed surface portions 38, 40 are formed which chamfer the edge portions of the circumferential edge 52 in this area in order to lower the stress peaks in this area of the nail portion. The cutter 56 can be moved in a direction parallel to the nail longitudinal axes to produce flattened lateral edges.

A similar surface preparation may be performed on outlet end 32 of bore 18.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An interlocking nail for fractures of a proximal femur comprising:
   a proximal portion, the proximal portion having a longitudinal axis and an outer surface extending parallel to the longitudinal axis;
   a circular bore through the outer surface extending at an angle less than 90 degrees to the longitudinal axis of the proximal portion; and
   the outer surface having recessed edge surface portions located on opposed sides of the bore, the recessed edge surface portions being flattened and rounded at a screw or pin inlet end, the flattened recessed edge surface portions being flattened along a plane perpendicular to a plane containing both the longitudinal axis of the nail and a central axis of the bore and parallel to the longitudinal axis of the nail proximal portion, and the recessed rounded edge surface portions being rounded on proximal and distal sides on the pin or screw inlet end around an axis transverse to the longitudinal axis and lying in a plane parallel to the plane of the flattened edge surface portions, the flattened recessed edge portions being intermediate the recessed proximal and distal rounded edge surface portions and forming a concave rounded edge open on first and second sides thereof.

2. A nail for insertion into a medullary canal of a long bone comprising:
   an elongated shank extending along a longitudinal axis;
   a circular bore extending through the elongated shank along an axis forming an angle less than 90 degrees with the longitudinal axis, the bore having an inlet end for receiving a bone fastener;
   an outer nail surface surrounding the inlet end;
   recessed flattened surfaces formed on the outer nail surface, the recessed flattened surfaces being in a plane perpendicular to a plane containing both the longitudinal axis of the nail and the axis of the bore and parallel to the longitudinal axis of the nail proximal portion; and
   recessed rounded surfaces formed on the opposite ends of the recessed flattened surfaces, each recessed rounded surface being rounded around an axis transverse to the longitudinal axis and parallel to the plane of the recessed flattened surfaces,
   the recessed flattened surfaces being intermediate the recessed rounded edge surface portions and forming a concave rounded edge open on the first and second sides thereof.

3. The nail of claim 2, wherein the recessed flattened surfaces form first and second sides of a notch in the outer nail surface surrounding said bore.

4. The nail of claim 3, wherein the recessed rounded surfaces on the outer nail surface surrounding said bore connect the ends of the recessed flattened surfaces.

5. The nail of claim 4, wherein the nail is a femoral nail.

6. The nail of claim 5, wherein the recessed rounded surfaces on the opposing ends of the recessed flattened surfaces extend along same direction.

7. The nail of claim 6, wherein an edge of each of the flattened surface adjacent the bore is rounded into the bore.

* * * * *